US005690109A

United States Patent [19]
Govind et al.

[11] Patent Number: 5,690,109
[45] Date of Patent: Nov. 25, 1997

[54] METHOD OF DESTRUCTIVE, NONINVASIVE HYPERPYREXIA OF TISSUES AND ORGANISMS UTILIZING NUCLEAR MAGNETIC RESONANCE

[76] Inventors: Rakesh Govind, 10409 Stone Ct., Cincinnati, Ohio 45242; Robert G. Loomis, 5500 Cody Rd., Independence, Ky. 41051

[21] Appl. No.: 493,924

[22] Filed: Jun. 23, 1995

[51] Int. Cl.$^6$ ............................ A61B 5/055; A61B 17/39
[52] U.S. Cl. .................. 128/653.2; 607/100; 607/154; 600/10; 324/315
[58] Field of Search .................. 128/653.2; 607/2, 607/96, 100, 101, 154, 155, 156; 600/2, 9–15; 324/315

[56] References Cited

U.S. PATENT DOCUMENTS

| | | |
|---|---|---|
| 3,789,832 | 2/1974 | Damadian . |
| 4,186,729 | 2/1980 | Harrison . |
| 4,190,053 | 2/1980 | Sterzer . |
| 4,240,439 | 12/1980 | Abe et al. . |
| 4,354,499 | 10/1982 | Damadian . |
| 4,411,270 | 10/1983 | Damadian . |
| 4,682,600 | 7/1987 | Haas et al. . |
| 4,823,813 | 4/1989 | Harrison . |
| 4,914,608 | 4/1990 | LeBihan et al. . |
| 4,951,688 | 8/1990 | Keren . |
| 4,979,512 | 12/1990 | Heubes . |
| 5,010,897 | 4/1991 | Leveen . |
| 5,014,699 | 5/1991 | Pollack et al. . |
| 5,080,102 | 1/1992 | Dory . |
| 5,090,423 | 2/1992 | Matsuda et al. . |
| 5,143,063 | 9/1992 | Fellner . |
| 5,148,814 | 9/1992 | Kikuchi et al. . |
| 5,163,446 | 11/1992 | Saitoh . |
| 5,183,456 | 2/1993 | Liboff et al. . |
| 5,203,782 | 4/1993 | Gudov et al. . |
| 5,224,492 | 7/1993 | Takahashi et al. . |

(List continued on next page.)

OTHER PUBLICATIONS

Water–Exchange, Electronic Relaxation, and Rotational Dynamics of the MRI Contrast Agent [Gd(DTPA–BMA)($H_2O$)] in Aqueous Solution: A Variable Pressure, Temperature, and Magnetic Field $^{17}$O NMR Study[1,2], Gabriel Gonzalez, et al., The Journal of Physical Chemistry, vol. 98, No. 1, pp. 53–59 (1994).

Two–dimensional spatially selective spin inversion and spin–echo refocusing with a single nuclear magnetic resonance pulse, Paul A. Bottomley et al., The Journal of Physical Chemistry, vol. 62, No. 10, pp. 4284–4290 (1987).

Innovation in San Francisco, John Travis, Science, vol. 257, p. 750 (1992).

Magnetic Resonance Imaging Can Cause Focal Heating in a Nonuniform Phantom, IEEE Transactions On BioMedical Engineering, vol. 40, No. 12, pp. 1324–1327 (1993).

Primary Examiner—Marvin M. Lateef
Assistant Examiner—Shawna J. Shaw
Attorney, Agent, or Firm—Frost & Jacobs

[57] ABSTRACT

A method of selectively heating targeted cells within a specimen while avoiding heating of non-targeted cells is provided. The method comprises the steps of:

(a) determining at least one combination of magnetic field strength and radio wave frequency (strength-frequency combination) at which only the targeted cells will resonate when the magnetic field and the electromagnetic radiation are applied to the specimen orthogonal to one another; and (b) applying a magnetic field and a radio frequency wave to the targeted cells, the strength of the magnetic field and the frequency of the radio wave corresponding to the strength-frequency combination to the targeted cells, in order to cause nuclear magnetic resonance in the targeted cells, thereby increasing the temperature of only the targeted cells.

16 Claims, 1 Drawing Sheet

U.S. PATENT DOCUMENTS

| | | |
|---|---|---|
| 5,225,282 | 7/1993 | Chagnon et al. . |
| 5,232,433 | 8/1993 | Kotsuka . |
| 5,236,410 | 8/1993 | Granov et al. . |
| 5,247,935 | 9/1993 | Cline et al. . |
| 5,251,629 | 10/1993 | Koizumi et al. . |
| 5,251,645 | 10/1993 | Fenn . |
| 5,261,405 | 11/1993 | Fossel . |
| 5,275,165 | 1/1994 | Ettinger et al. . |
| 5,284,144 | 2/1994 | Delannoy et al. . |
| 5,291,890 | 3/1994 | Cline et al. . |
| 5,307,812 | 5/1994 | Hardy et al. . |
| 5,318,031 | 6/1994 | Mountford et al. . |
| 5,323,778 | 6/1994 | Kandarpa et al. . |
| 5,323,779 | 6/1994 | Hardy et al. . |
| 5,364,392 | 11/1994 | Warner et al. . |
| 5,462,055 | 10/1995 | Casey et al. . |
| 5,507,743 | 4/1996 | Edwards et al. . |
| 5,584,863 | 12/1996 | Rauch et al. . |

METHOD OF DESTRUCTIVE, NONINVASIVE HYPERPYREXIA OF TISSUES AND ORGANISMS UTILIZING NUCLEAR MAGNETIC RESONANCE

BACKGROUND OF THE INVENTION

1. Field of the Invention

The present invention relates to the use of hyperthermia in the destruction of tissues and other organisms, and more particularly to a method for selectively delivering hyperthermic power to targeted tissues or organisms while avoiding surrounding, non-targeted tissues or organisms.

2. Description of Related Art

Approximately one-fifth of all deaths in the United States are due to cancer, and an estimated $20 billion per year is spent on the care and treatment of cancer patients. It is generally acknowledged that early recognition and treatment of cancer is paramount to successful results. The most common, modem-day method of treating cancer is surgical intervention to remove both primary and metastatic tumors. It is also well-known that some malignant tumors, particularly lymphomas, leukaemias and carcinomas can be treated by radiation therapy using gamma rays. Recently, advances have also been made in the use of chemotherapeutic agents, often in conjunction with surgical and/or radiation treatment. In addition, immunotherapeutic techniques have been developed which utilize antibodies to which cytocidal agents are linked, and these techniques have met with limited success.

It is known that cancer cells die at 43.5° C. within 90 minutes and that normal cells will survive at temperature as high as 45.5° C. for 90 minutes. In fact, as far back as 5,000 years ago, hyperpyrexia of the human body at 44° C. was practiced in China for periods as long as two hours in an attempt to treat cancer and other diseases. Most of the patients, however, could not withstand such temperatures over this period of time and died. More recently, a method for treating malignant tumors by local hyperpyrexia using an electromagnetic field has been developed (*Application of Hyperpyrexia and Hyperglycemia in Treating Malignant Tumors*, Meditsina Publishing House, Moscow, pp. 91–95, 1980). Alternating electromagnetic radiation in a microwave band is used to achieve local hyperpyrexia of the neoplasm. However, this method is limited to the treatment of surface malignant tumors, with a maximum depth of 2 cm, due to the non-uniform heating of the tissue.

Hyperthermic therapy can also be accomplished using probes or applicators such as that described in U.S. Pat. No. 4,823,812 to Eschel et al. (the "Eschel Applicator"). The Eschel Applicator is inserted into body cavities and includes a microwave antenna which generates radio frequency electromagnetic radiation for heating the body tissue. An "Eschel Probe" containing thermocouples (U.S. Pat. No. 4,813,429) is used to measure the heat produced by the Eschel applicator so as to control the hyperthermic therapy. Single probes capable of imaging the tissues for control of the therapy, locating the therapy device and delivering the hyperthermic therapy have also been disclosed (U.S. Pat. No. 5,323,778). Other methods of achieving hypothermia include catheterization of the arterial vessel that feeds the tumor, and administration of a suspension of ferromagnetic material with simultaneous application of a local magnetic field onto the area of the tumor (U.S. Pat. No. 5,236,410). Hyperthermia is created by subjecting the minor to an ultrahigh radio frequency electromagnetic field or ultrasonic waves to produce heating of the tumor. All of these techniques however, involve invasive procedures requiring the insertion of various probes or the administration of specific solutions, which are problematic when the tumorous tissues are in a critical area of a vital organ.

Noninvasive hyperthermia methods for treating tumors deep within the body have also been developed. The methods utilize phased-array antennas for focussing the radio frequency energy on the tumorous tissue, thereby generating free induction decay signals. These techniques have utilized a magnetic resonance scan sequence in order to obtain signals from the tumorous tissue, and these signals are in turn used to determine the proper phase and amplitude to be applied to each element of the phased-array antenna in order to focus the RF signals (U.S. Pat. No. 4,951,688). Previous methods using phased-array antennas had employed invasive techniques of inserting probes to determine the relative phase of excitation in each individual element of the array (Optimal Temperature Control System with Phased-Array Hyperthermia System, IEEE Transactions on Microwave Theory and Techniques, Vol. MTT-34, No. 5, May 1986). Phased-array antennas, however, are only capable of focussing the RF energy within a specified volume, and are not specifically directed towards the malignant cells. Thus, these methods are only of limited use.

Other non-invasive treatment techniques which have been developed involve the use of fluctuating magnetic fields (U.S. Pat. No. 5,183,456), which are used either in conjunction with chemotherapeutic agents for reducing malignancy or by potentiating differentiation of the cells. This method either requires the use of specific chemotherapeutic agents which have many drawbacks, or simply inhibits malignancy. Tumors have been also selectively destroyed in cancer subjects using focussed ultrasound heating (Billard, B. E., Hynynen, K., Roemer, R. B., Effects of Physical Parameters on High Temperature Ultrasound Hyperthermia, Ultrasound in Med. & Biol., vol. 16, No. 4, pp. 409–420, 1990). Recently, magnetic resonance temperature sensitive pulse sequences (as described in U.S. Pat. No. 4,914,608), have been applied in conjunction with ultrasound heating in order to accurately localize the heat (U.S. Pat. No. 5,275,165).

Thus, there is a need for a method of non-invasively and selectively heating targeted cells (i.e., targeted tissues and/or organisms) to achieve destruction, while not affecting the surrounding, non-targeted tissues and/or organisms

SUMMARY OF THE INVENTION

The foregoing objects can be accomplished by providing a method of selectively heating targeted cells within a specimen, comprising the steps of:

(a) determining at least one combination of magnetic field strength and radio wave frequency (strength-frequency combination) at which said targeted cells will resonate when said magnetic field and said electromagnetic radiation are applied to said specimen orthogonal to one another; and (b) applying a magnetic field and a radio frequency wave to said targeted cells, the strength of said magnetic field and the frequency of said radio wave corresponding to said strength-frequency combination to said targeted cells, in order to cause nuclear magnetic resonance in said targeted cells, thereby increasing the temperature of said targeted cells.

The specimen will also likely comprise non-targeted cells, and the non-targeted cells should not resonate significantly when said strength-frequency combination is applied to them, so that said non-targeted cells will not be appreciably heated by said applying step. The radio frequency wave is applied in the form of a pulse, and preferably a plurality of RF pulses are applied to said specimen in order to increase the heating effect. The interval between each of said pulses is less than the relaxation time $T_1$ of said targeted cells, preferably approximately one third of $T_1$. A plurality of said strength-frequency combinations are also preferably determined and applied to said targeted cells.

The specimen may be a live mammal (such as a human patient), and the targeted cells may comprise tumor cells or gland cells. The step of determining appropriate strength-frequency combinations may be accomplished by magnetic resonance imaging of said targeted cells. Alternatively, the targeted cells may be bacteria. Preferably, the selective heating of the present invention is sufficient to destroy the targeted cells. In addition, a relaxation enhancement agent may be administered to prior to performing the above method in order to enhance the heating effect. Such agents may include known fluorocarbons.

DESCRIPTION OF THE PREFERRED EMBODIMENTS

Figure 1:
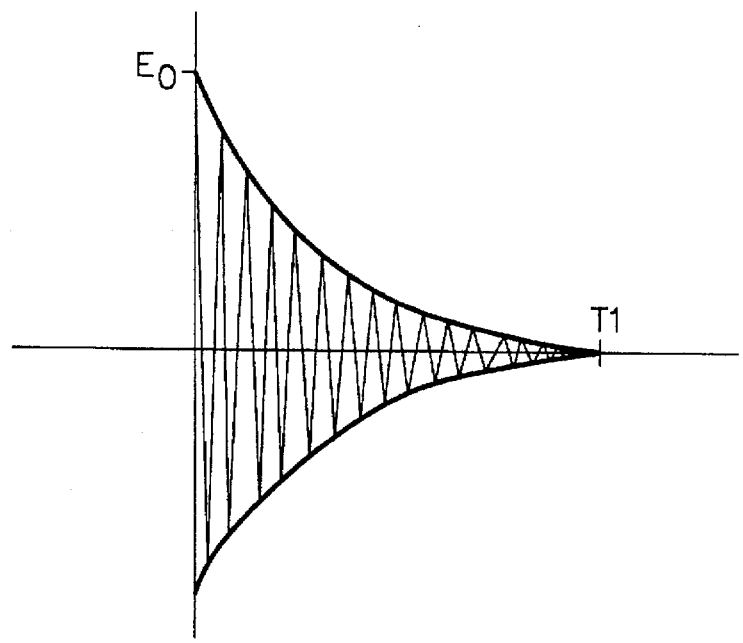
FIG. 1 is a schematic of the energy released during relaxation following application of a single RF pulse during the nuclear magnetic resonance method of the present invention.

While hyperpyrexia of tumorous tissue itself is not new, the targeted tissues are usually surrounded by healthy tissue, and thus any method employed must protect the healthy tissue while destroying the tumorous tissue. Applicants have now found that nuclear magnetic resonance can be used to selectively heat the targeted tissues, while maintaining the non-targeted tissues at a much lower temperature. In this fashion, the targeted tissue, and, as will be discussed later, certain targeted organisms (such as bacteria), can be heated to a point where the cells of the targeted body will be destroyed without adversely affecting the surrounding healthy tissue. Standard MRI equipment can be employed, with some minor modifications. Thus, the apparatus necessary for practicing the methods of the present invention includes a magnetic field generator for producing a controlled, intermittent, directionally-oriented magnetic field parallel to a predetermined axis through the targeted area (e.g., a malignant neoplasm). Magnetic resonance can then be achieved by applying a radio frequency perturbation signal perpendicular to this magnetic field (as a pulse). An imaging coil is also typically provided, and includes a coil body and coil tip. As is known in the art, the imaging coil can also be adjusted to select particular frequencies which are of interest (i.e., a tuneable coil). When the radio frequency (RF) signal is applied at the proper frequency, certain protons will deflect from their normal aligned states to a higher-energy state by means of nuclear magnetic resonance absorption. When the RF signal is turned off, the protons which have been flipped will return to their normal state, and will emit a decaying RF signal. This RF signal will decay to a zero amplitude during the time period $T_1$ (spin-lattice relaxation time).

In vitro measurements in rats (Damadian, R., *Tumor Detection by NMR*, Science 171: 1151–1153, 1971) and later in human beings (Damadian, R., Zaner, K., Hor, D. et al., *Human Tumors detected by NMR*, Proc. Nat. Acad. Sci. U.S.A. 71: 1471–1473, 1974; Eggleston, J. C., Hazelwood, C. F., Cleveland, G., et al., *NMR Studies of several experimental and human malignant tumors*, Cancer Research 33: 2156–2160, 1973) have shown that differences in NMR $T_1$ relaxation times between normal and cancerous tissues exist. These differences in relaxation times, in fact, led to the development of magnetic resonance imaging (MRI) technology, which can be utilized to not only detect tumors in the body, but also to image other structures within the body. Subsequent studies have also shown, however, that as the protons of the tissue "relax" from the spin state to their lower-energy lattice state, heat is released to the protons' surroundings. Thus, tissues whose protons have been forced into resonance by application of the appropriate magnetic field and perpendicular radio waves, will experience a rise in temperature.

In addition to unique relaxation times, the protons within various cell environments in the body will only deflect from their normal aligned states to a higher-energy state at a specific combination of magnetic field strength and radio wave frequency. MRI, however, utilizes a broad range of radio wave frequencies to provide a complete image. By a proper selection of radio wave frequency and magnetic field strength, only the protons in targeted cells (e.g., tumor cells) will be deflected into the higher energy state, while the non-targeted cells are not affected. This may be readily accomplished using standard MRI techniques, however only specific radio wave frequencies are employed. It is also likely that a tumor cell, for example, will exhibit several distinct resonant radio wave frequencies suitable for use in treatment. Once the applicable frequencies are determined for a particular targeted tissue, the protons of the targeted tissue can be caused to resonate at one or more of these frequencies, thereby resulting in a release of heat within the tissue. Since the protons of the non-targeted tissues will not resonate at the chosen frequencies, these non-targeted tissues will not be heated.

By using the methods of the present invention, the targeted cells can be heated to the desired temperature for the appropriate period of time, thereby destroying the targeted cells while not affecting the surrounding non-targeted areas. These methods may also be combined with the injection of agents that specifically bind to the targeted cells to promote the heating effect. In addition, the hyperthermia of the present invention may also be combined with ionizing radiation treatment, since the hyperthermia will promote the absorption of radiation by the targeted cells. In order to monitor the temperature increases of the targeted tissues, traditional magnetic resonance imaging may be employed to ensure that the proper temperature and duration is achieved. Alternatively, the apparatus and methods disclosed in U.S. Pat. Nos. 5,307,812 or 4,190,053, which are herein incorporated by reference, may be employed to monitor the temperature of the targeted tissues.

The Lamor theorem provides an easy way to determine the precessional frequency $v$ of any particular nuclei in a magnetic field of a given strength (H):

$$v=(\gamma/2\pi)H$$

where $\gamma$ is a constant called the magnetogyric ratio, which has a specific value for each atomic nucleus. The process by which energy is lost to the lattice is called "relaxation" and is characterized by two time constants, $T_1$ and $T_2$. $T_1$ is called the thermal relaxation, or spin-lattice relaxation time, and as $T_1$ decreases greater amounts of energy can be transferred to the lattice thereby resulting in an increased heating effect during relaxation. $T_2$ is known as the spin-spin relaxation time, and the energy released during $T_2$ relaxation is much less than $T_1$.

While radio frequency fields in magnetic resonance imaging cause heating of the tissues, the energy deposited by standard MRI examinations poses no threat to human health. However, if certain cells (such as cancerous tumors) are targeted by a precise selection of the radio frequency or frequencies employed, localized heating of the targeted cells can be accomplished. Thus, since the non-targeted tissue is not heated, application of the radio frequency (or frequencies) field can be repeated (if necessary) until the targeted tissue is heated to the point of destruction of all or a portion of the targeted cells, or at least until subsequent growth of the targeted cells is inhibited.

Relaxation Enhancement Agents for Increased Hyperthermic Effect

Relaxation enhancement agents can also be utilized in order to permit the transfer of increased amounts of energy to the targeted tissue, thereby resulting in an enhanced heating effect. The extent of hyperthermia is a complex function of the type of enhancement agent used and the location and size of the minor or other cells subjected to NMR treatment. The extent of energy transfer, however, can be enhanced by decreasing the relaxation time $T_1$ of the targeted tissue. Enhancing agents that decrease $T_1$ substantially are preferred in his embodiment. One such class of agents are fluorocarbons that exhibit extremely low $T_1$ values. Fluorocarbons are known to dissolve substantial amounts of air and hence oxygen, and therefore these agents are selectively transported to tumors that have increased metabolic rates or oxygen consumption. By injecting these fluorocarbons in patients, the fluorocarbons will be concentrated in the targeted tumor or other cells. In fact, these substances are often employed to enhance imaging during MRI. Thus, an increased hyperthermic effect can be achieved in tumorous tissues by administering these agents prior to treatment.

Cyclic Radio Frequency Excitation for Enhanced Hyperthermia Effect

When a single pulse of radio frequency energy is applied to the targeted cells using the method of the present invention, the extent of heating will often be rather limited. The temperature rise also results in an increased blood flow to the area in an attempt to decrease the temperature back to a normal condition, thereby further limiting heating. The blood flow response, however, is much slower than the temperature rise caused by the magnetic resonance. Because of these two factors, a single pulse of RF energy will usually only result in a temperature rise in the range of 0.1 degrees to 2 degrees C., which is generally insufficient to affect the targeted cells. While repeating the process after time period $T_1$ will improve the heating effect, blood flow to the area will still limit the temperature rise. Applicants have found, however, that the energy transfer (i.e., the temperature increase) which occurs when the protons relax from the spin to the lattice states can be enhanced by the cyclic excitation of the radio frequency coil. The resulting increased energy transfer allows for the increased dissipation of energy as heat.

As mentioned previously, when a radio frequency signal at a specific frequency is applied, the resonating protons deflect from their aligned states to a higher-energy state through the absorption of energy. After the radio frequency signal is turned off, all of the protons relax back to the aligned, equilibrium state. This realignment or "relaxation" in the direction of the magnetic flux is usually described by a specific relaxation time, denoted by $T_1$. As $T_1$ decreases, increased energy transfer occurs between the spin and lattice states, which results in an increased temperature rise of the surrounding tissue. $T_1$, however, is characteristic of a water molecule in a specific cell environment and can be modified only by the application of external agents. A typical relaxation curve for energy dissipation is shown in FIG. 1 wherein the energy release is plotted versus time. It should be noted that the relaxing protons emit RF energy which accounts for the resonating frequency as shown in FIG. 1. The energy release rate can be quantified as follows:

$$E(t) = E_0 e^{(-\frac{at}{T_1})} \qquad (1)$$

where a is a constant, $T_1$ is the relaxation time, and Eo is the initial energy transfer rate at time t=0, before the radio frequency signal is turned off. The total energy transferred ($E_{total}$) can be found by integrating the above equation from t=0 to t=$T_1$, and is given by:

$$E_{total} = \left( \frac{T_1 E_0}{a} \right)(1 - e^{(-a)}) \qquad (2)$$

Hence the total energy transferred increases as the constant a decreases.

Figure 2:
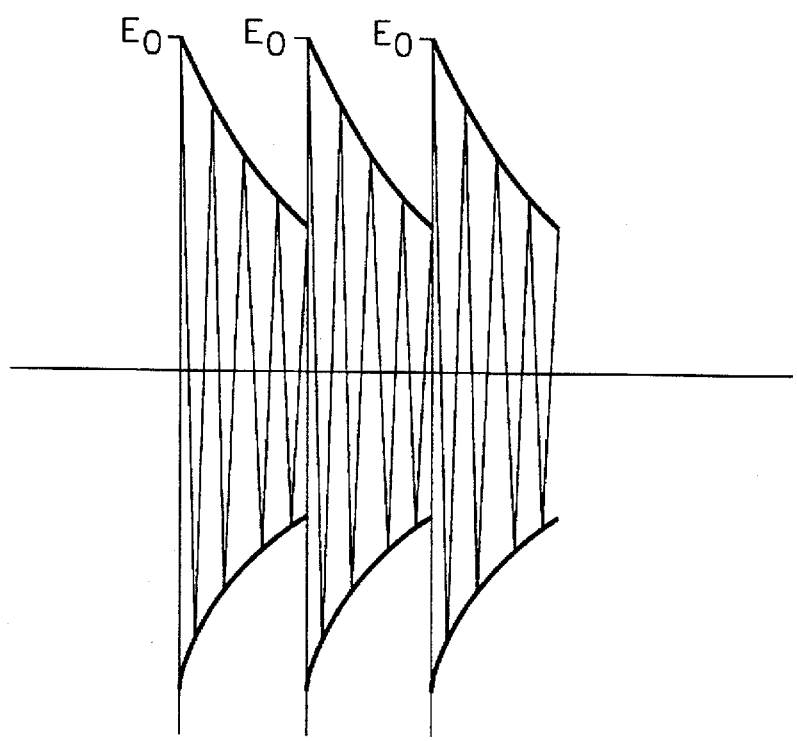
FIG. 2 is a schematic of the energy released during relaxation following the cyclic application of an RF pulse during the nuclear magnetic resonance method of the present invention.

In order to increase the amount of energy transferred, the radio frequency energy is applied cyclically. In other words, pulses of radio frequency are repeatedly applied at intervals which are a fraction of time $T_1$ (as shown in FIG. 2). In this fashion, the total energy transferred will thus increase as the number of cycles is increased, since the majority of the energy is released during the initial stages of relaxation. This is evident from the following equation for total energy transfer, when the radio frequency pulses are applied cyclicly, wherein n is the number of times the radio signal is applied:

$$E_{tc} = \left( \frac{n T_1 E_0}{a} \right)\left( 1 - e^{(-\frac{a}{n})} \right) \qquad (3)$$

The ratio of the energy transferred using the cyclic RF pulses signal and the total energy transferred when a single pulse is applied and then permanently switched off (i.e., ratio of equations (3) and (2)) is given by:

$$\text{Ratio} = \frac{n\left(1 - e^{(-\frac{a}{n})}\right)}{(1 - e^{(-a)})}$$

The above ratio is equal to 1 when n=1, i.e., only one cycle during the relaxation time $T_1$. However, as n is increased, the ratio increases above a value of 1, indicating that increased energy transfer can occur as the number of cycles are increased. This in turn will result in enhanced heating of the targeted tissue such that the desired temperature can be reached.

The temperature increase when cyclic radio frequency excitation is employed is also increased due to the fact that the blood flow response is not nearly as fast as the transfer of energy. In other words, while blood flow to the targeted area will increase as energy is released to the surrounding tissue, cyclic application of the RF pulses will permit the temperature increase of the targeted tissue to remain one step ahead of the blood flow response. This in turn will result in a much greater temperature increase, thereby permitting the destruction of the targeted cells. Thus, an increased heating effect is obtained when the interval between pulses is less than $T_1$ as compared to when the interval between pulses is equal to or greater than $T_1$. Preferably, the interval between pulses is approximately equal to one-third of $T_1$.

The methods of the present invention, while capable of heating the targeted cells to temperatures which will achieve destruction, may also be used in conjunction with other therapies. This is particularly true because of the cost of the magnetic resonance treatment of the present invention. Since the magnetic coils utilized in the treatment process of the present invention utilize liquid helium which is lost over time, each treatment can be extremely expensive. The method of the present invention, however, can be employed to destroy the remaining portion of a cancerous tumor remaining after surgical procedures have been employed to remove the bulk of the tumor. The methods of the present invention can also be employed to reduce the size of a tumor to the point where pharmaceutical agents or even the patients own natural immunity will eliminate the remainder of the tumor. The hyperthermic effect of the present invention may even be used in conjunction with chemotherapy or ionizing radiation treatments, since in many cases the increased temperature of the targeted tissue will result in an increased absorption of radiation or chemotherapeutic agents. The method of the present invention may also be employed to merely inhibit the growth of the targeted cells, as the hyperthermic treatment may cause the targeted cells to cease further growth.

In order to demonstrate the effectiveness the methods of the present invention, the following experiments were conducted using standard MRI equipment.

EXAMPLE 1

Rat tissue cells were grown in agar medium in an 8 cm×2 cm test tube. The cells were incubated at 27° C. for 22 days in order to increase the concentration of cells present in the medium. The test tube was then placed in the MRI equipment, and resonant frequency responses were measured at 1.5 Mhz, 2.2 MHz, 3.4 MHz, 5.6 MHz and 7.3 MHz for a magnetic field strength of 1.5 Tesla. The frequencies were found to exist as narrow bands having a band width of approximately 0.2 MHz, which was far smaller than the separation. The band width is likely due to the fact that different parts of the cell may be responsible for each frequency, and the fact that the resonant frequencies tend to change slightly as the temperature of the cells increase. It should be noted that several other higher resonant frequencies were observed. However these values were discarded due to problems with heating of the radio frequency coil at these higher frequencies.

EXAMPLE 2

Cancerous rat tissue cells were grown in an agar medium in an 8 cm×2 cm test tube. The cells were incubated in 27° C. for about 15 days to increase the concentration. The test tube was then placed in the MRI system, and resonant frequencies were measured at 0.98 MHz, 2.2 MHz, 4.3 MHz, 5.6 MHz, 7.3 MHz, and 8.8 MHz. Thus, it was clear that there were several frequencies which elicited a resonance response in the cancer cells but not in the normal cells.

EXAMPLE 3

A single frequency generator was attached to the radio frequency coil of the MRI equipment in order to provide a single assigned frequency at varying amplitudes. A single radio frequency of 0.98 MHz was chosen, as only the cancerous tissue cells previously observed a resonance response at this frequency. The lowest of such frequencies was chosen in order to minimize any heating of the RF coil during the process, since the coil was only cooled by air. In normal practice, the phased antenna coil would be water cooled in order to avoid this problem. A thermocouple was placed in the cell medium in order to precisely measure increases in temperature. When radio frequency pulses of 0.98 MHz were applied cyclically to the cancerous cells, a steady-state temperature increase of 9° C. was observed only two minutes after the RF pulse was applied. The RF pulses were applied at an interval of one-third of relaxation time $T_1$. When this same cyclic RF energy was applied to normal tissue cells, however, a temperature increase of only 1° C. was observed.

These examples clearly demonstrate that selective heating of targeted cells may be obtained by applying a radio frequency signal which produces a resonance response in the cancerous cells but not in normal tissue cells. A 9° C. temperature increase was observed, and the heating effect can be further improved by applying multiple resonant radio frequency signals rather than the single frequency in the above examples. It should also be noted that upon heating, a change in relaxation time will occur and the resonating frequency will decrease somewhat. Thus, it may also be necessary to monitor the heating and resonance to determine whether or not a change in the radio frequency in order to continue heating of the hottest tissue when multiple RF pulses are employed. In addition, it should be noted that multiple treatments may be used to destroy further amounts of the targeted cells, and other treatment methods may be employed with the methods of the present invention.

In order to implement the method of the present invention, a modified MRI system may be readily employed. One or more selective frequency generators capable of generating precise radio frequencies may replace the variable frequency generator commonly employed in MRI systems. More than one frequency generator may be used, so that multiple selected frequencies may be applied to the patient at any one time in order to further enhance the heating. A high speed electronic switch is connected to the frequency generators which allows the frequencies to be applied intermittently, rather than as a single pulse. Optionally, MRI temperature-monitoring techniques may simultaneously be employed in order to monitor the temperature of the targeted tissues noninvasively, and to optimize the resonant frequencies employed so as to maximize the temperature increase of the targeted cells. The selective frequency generators and electronic switch for intermittent application can be readily added to existing MRI apparatus, thereby decreasing the total cost of the apparatus for performing the methods of the present invention.

While the foregoing methods are particularly suited for the destruction of tumors and the like, these same methods can be used to destroy or inhibit the growth of other types of cells. For example, glands (such as enlarged prostate glands) may be reduced in sized using the hyperthermic treatment methods of the present invention. Although this may require several treatments, the methods of the present invention are harmless to the non-targeted cells and thus repeat treatments will not be problematic. These methods can also be used to destroy bacteria such as *e-coli* and numerous others, since the cells of each of these organisms will also resonate at their own particular frequencies. These bacteria can be destroyed in the animal host, or the methods of the present invention can even be applied to the bacteria existing outside of an animal host.

Since bacteria and other simple organisms will exhibit unique resonance frequencies, the methods of the present invention can also be employed to create a "catalog" of nuclear magnetic resonance characteristics for these organisms. Thus, when a given magnetic field strength is applied, the radio frequencies which cause resonance in these organisms can be readily determined and catalogued for later use. Identification of organisms can be applied to biological environmental treatment in order to monitor the types of organisms present. In addition, the temperature at which these organisms are destroyed can also be readily determined. The measurement of relaxation times at the various frequencies will also aid in identification. In this fashion, the methods of the present invention can even be used to identify the presence of these organisms in or outside of an animal host. If the resonant frequencies and relaxation times are measured for a particular sample, these values can be compared to known parameters in order to identify the organisms present in the sample.

These principles can also be extended to analysis of DNA, as each particular DNA will exhibit unique resonant frequencies and relaxation times. By matching frequencies and relaxation times for DNA samples, identification of the unknown DNA can be accomplished. The results can be used in medical treatment or even criminology, and the methods are much simpler and cheaper than those currently available (such as a PCR gene probe).

What we claim is:

1. A method of selectively heating targeted cells within a specimen, comprising the steps of:
   (a) determining at least one combination of magnetic field strength and radio wave frequency (strength-frequency combination) at which said targeted cells will resonate when said magnetic field and said electromagnetic radiation are applied to said specimen orthogonal to one another; and
   (b) applying a magnetic field and a radio frequency wave to said targeted cells, the strength of said magnetic field and the frequency of said radio wave corresponding to said strength-frequency combination to said targeted cells, in order to cause nuclear magnetic resonance in said targeted cells, thereby increasing the temperature of said targeted cells.

2. The method of claim 1, wherein said specimen also comprises non-targeted cells, and wherein said non-targeted cells do not resonate significantly when said strength-frequency combination is applied to them, so that said non-targeted cells will not be appreciably heated by said applying step.

3. The method of claim 2, wherein said radio frequency wave is applied in the form of a pulse.

4. The method of claim 3, wherein a plurality of RF pulses are applied to said specimen.

5. The method of claim 4, wherein the interval between each of said pulses is less than the relaxation time $T_1$ of said targeted cells.

6. The method of claim 2, wherein a plurality of said strength-frequency combinations are determined and applied to said targeted cells.

7. The method of claim 2, wherein said specimen is a live mammal, and wherein said targeted cells comprise tumor cells.

8. The method of claim 5, wherein said specimen is a live mammal, and wherein said targeted cells comprise tumor cells.

9. The method of claim 2, wherein said determining step is accomplished by magnetic resonance imaging of said targeted cells.

10. The method of claim 2, wherein said specimen is a live mammal, and wherein said targeted cells comprise gland cells.

11. The method of claim 2, wherein said targeted cells are bacteria.

12. The method of claim 2, wherein said heating results in the destruction of said targeted cells without harming said non-targeted cells.

13. The method of claim 2, wherein a relaxation enhancement agent is administered to said specimen prior to said applying step.

14. A method of hyperthermically destroying targeted cells within a specimen while not harming non-targeted cells, comprising the steps of:
   (a) determining at least one combination of magnetic field strength and radio wave frequency (strength-frequency combination) at which said only said targeted cells will resonate when said magnetic field and said electromagnetic radiation are applied to said specimen orthogonal to one another; and
   (b) applying a magnetic field and a radio frequency wave to said targeted cells, the strength of said magnetic field and the frequency of said radio wave corresponding to said strength-frequency combination determined in step (a) to said targeted cells, in order to cause nuclear magnetic resonance in said targeted cells, thereby increasing the temperature of said targeted cells to an extent that they are destroyed.

15. The method of claim 14 wherein said radio frequency wave is applied in the form of a plurality of pulses, the interval between each of said pulses being less than the relaxation time $T_1$ of said targeted cells.

16. The method of claim 15, wherein said specimen is a patient, and said targeted cells comprise tumor cells.

* * * * *